United States Patent [19]

Schulman

[11] Patent Number: 5,460,523
[45] Date of Patent: Oct. 24, 1995

[54] DENTAL COMPOSITE CARTRIDGE

[75] Inventor: Martin Schulman, Orange, Conn.

[73] Assignee: Jeneric/Pentron, Wallingford, Conn.

[21] Appl. No.: 274,685

[22] Filed: Jul. 14, 1994

[51] Int. Cl.$^6$ ..................................................... A61C 5/04
[52] U.S. Cl. .......................................................... 433/90
[58] Field of Search .................................. 433/80, 82, 89, 433/90; 222/386

[56] References Cited

U.S. PATENT DOCUMENTS

| | | | |
|---|---|---|---|
| 4,391,590 | 7/1983 | Dougherty | 433/90 |
| 4,767,326 | 8/1988 | Bennett et al. | 433/90 |
| 4,963,093 | 10/1990 | Dragan | 433/90 |
| 4,969,816 | 11/1990 | Drumm | 433/90 |
| 5,061,179 | 10/1991 | Dragan | 433/90 |
| 5,083,921 | 1/1992 | Dragan | 433/90 |
| 5,100,320 | 3/1992 | Martin et al. | 433/90 |
| 5,122,057 | 6/1992 | Discko, Jr. | 433/90 |
| 5,125,836 | 6/1992 | Dragan et al. | 433/90 |
| 5,129,825 | 7/1992 | Discko, Jr. | 433/90 |

*Primary Examiner*—Ren Yan
*Attorney, Agent, or Firm*—Watson, Cole, Grindle & Watson

[57] ABSTRACT

A dental composite cartridge is made of a plastic material molded to define an elongated cylindrical hollow body portion forming a reservoir, and a discharge nozzle portion. A piston is disposed within an open end of the hollow body after the body is filled with dental composite material. The hollow body and the discharge nozzle define a planar end wall which intersects the longitudinal axis of the hollow body at an angle of about 45°. The interior design of the hollow body and its angled planar end wall enables a simple, easy to manufacture and cost-effective piston to be used in the hollow body for discharging dental composite material from the reservoir.

14 Claims, 1 Drawing Sheet

DENTAL COMPOSITE CARTRIDGE

FIELD OF THE INVENTION

The present invention relates to a cartridge for dispensing dental composite materials and designed to fit within a complementary seat of a dental composite cartridge gun.

BACKGROUND OF THE INVENTION

Dental composite cartridges and ejector-type applicators have been developed to provide an easy method of handling uncured dental composite. Small cartridges which can hold single dosages or only a few dosages of composite have also been developed for obvious sanitation and economic reasons.

One such cartridge is disclosed in U.S. Pat. No. 4,391,590 which relates to a cartridge having one end of a cylindrical hollow body closed by a hemispherical wall. The hemispherical wall has substantially the same uniform thickness as the body. The piston within the body has a complementary inner end which is also hemispherical in shape. The cartridge includes a color-coded cap on its nozzle end to indicate desired properties of the contents of the cartridge.

U.S. Pat. No. 4,963,093 relates to a cartridge having a blunt internal end wall, an internal conically shaped wall surface tapering toward the closed end of the cartridge, and a complementary conical piston. An internal frusto-conical chamber tapering toward the closed end of the cartridge and in open communication with a reservoir portion is also provided.

U.S. Pat. No. 5,129,825 relates to a cartridge or capsule comprising a body portion having a series of circumferentially spaced longitudinally extending ribs. The ribs function to resist any internal build-up of pressure that may be developed during the extrusion of the material from the capsule.

Various problems exist in the above-mentioned cartridges. Most require a complicated and relatively expensive body and piston, and some pistons comprise more than one part, for example, a piston proper and a sealing ring. Most pistons have complicated pressure end surfaces which require the piston to be molded. A need therefore exists for a simple yet effective dental composite cartridge which is relatively inexpensive and easy to manufacture.

SUMMARY OF THE INVENTION

It is an object of the present invention to provide a dental composite cartridge which is simple, easy to manufacture, and inexpensive. These and other objectives are achieved according to the present invention by providing a dental composite cartridge made of a plastic material molded to define an elongated cylindrical hollow body reservoir portion having an interior planar end wall, and a discharge nozzle portion. The cylindrical hollow body is provided with an open end opposite the end wall having an annular, relatively short circular exterior flange designed to fit in a corresponding seat of an ejector-type holder or gun. A piston is disposed within the open end of the hollow body after the body is filled with dental composite material.

The planar end wall intersects and is angled with respect to the longitudinal axis of the hollow body, preferably at an angle of about 45°. The interior design of the hollow body and the angled planar end wall enables an extremely simple and cost-effective piston to be used in the hollow body. The piston can be made by simply cutting a short section of a rigid plastic cylindrical dowel at an angle with respect to the longitudinal axis of the dowel. There is no need to mold the piston of the present invention, but rather, it can be cut from a stock plastic rod. Due to the angled planar surface of the piston pressure end, the piston will right itself in the hollow body if it rotates therein, upon contact with the complementary planar end wall. The simple design enables an almost complete expulsion of expensive dental composite material from the cartridge when the piston is fully plunged by an ejector-type holder or gun.

BRIEF DESCRIPTION OF THE DRAWINGS

The invention may be more fully understood with reference to the accompanying drawings, wherein.

DETAILED DESCRIPTION OF THE INVENTION

Figure 1:
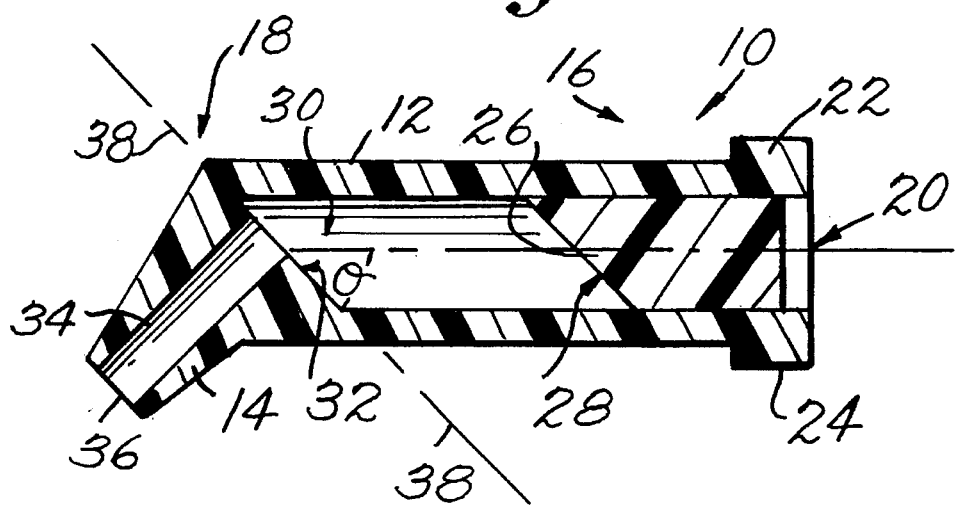
FIG. 1 is a cross-sectional schematic view of a dental composite cartridge according to the present invention.
Figure 2:
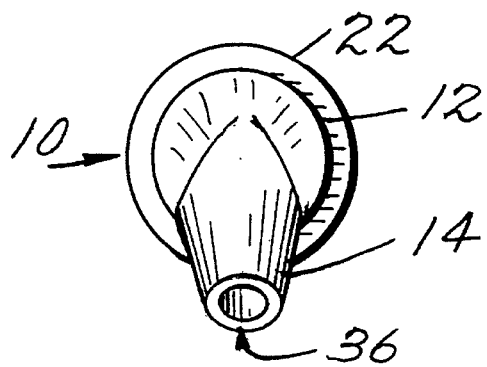
FIG. 2 is an end view of a cartridge according to the present invention.

FIG. 1 shows a cross-sectional schematic view of a cartridge 10 according to an embodiment of the present invention. The cartridge 10 is made of a plastic material molded to define an elongate cylindrical hollow body 12 and a discharge nozzle 14. The body 12 has an open end 16, and a discharge end 18. The discharge end 18 is joined to the discharge nozzle 14.

Figure 3:
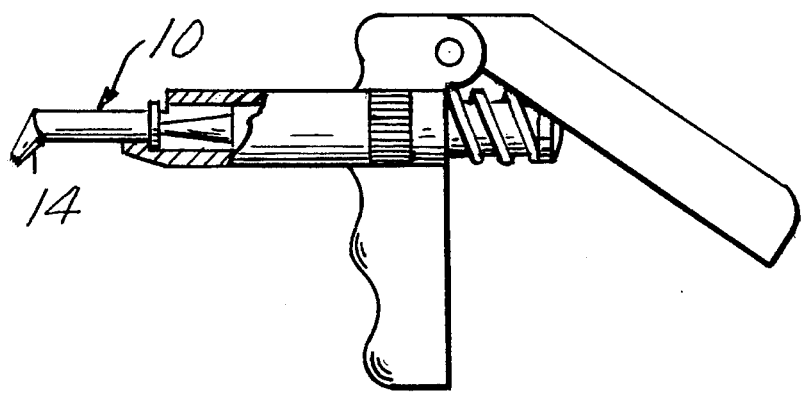
FIG. 3 a perspective view of the cartridge shown in FIG. 1 inserted into a conventional cartridge gun.

The open end 16 of the body 12 includes an opening 20 and an annular, relatively short, circular exterior flange 22 of limited width and having a smooth and continuous outer surface 24. The flange 22 is designed to fit in a corresponding seat of an ejector-type holder such as a cartridge gun, as shown in FIG. 3.

A piston 26 is disposed within the open end 20 of the body 12 after the body 12 has been filled with dental composite material (not shown). The piston 26 comprises a short, substantially cylindrical piece of rigid plastic material. A pressure end 28 of the piston 26 is formed by cutting or molding the material to form a planar end surface which intersects the longitudinal axis of the cylindrical piece at an angle. The angle relative to the longitudinal axis of the body 12 is preferably about 45°, or the same as angle Θ, described below.

The diameter of the cylindrical piece is Just slightly less than the diameter of the interior cavity or reservoir 30 of the body 12 to provide a very close fit yet allow sliding movement of the piston 26 within the reservoir 30.

The intersection of the discharge end 18 of the body 12, and the discharge nozzle 14 defines a planar end wall 32. The planar end wall intersects the body 12 at an angle Θ relative to the longitudinal axis of the body 12. Θ can be selected from 30° to 60° according to one embodiment of the invention, from 35° to 55° according to another embodiment, and from 40° to 50° according to yet another embodiment. In a preferred embodiment, such as the one shown in FIG. 1, Θ is 45°.

The discharge nozzle 14 extends away from the body 12 at an angle, also preferably about 45°, and away from the planar surface of the end wall 32. In the embodiment shown, the discharge nozzle extends away from the planar surface of the end wall 32 at a 90° angle. The discharge nozzle 14 defines a substantially cylindrical communication or discharge channel 34 between a discharge opening 36 and the reservoir 30 of the hollow body. The outer diameter of the discharge nozzle 14 continuously tapers from its intersection with the body 12 to the discharge opening 36, as shown along line 38.

According to the invention, the planar internal end wall surface may have an elliptical shape and likewise a major axis along the ellipse. The elliptically-shaped internal end wall surface intersects the generally cylindrical hollow body at two points along the major axis, defined herein as the proximal point and the distal point with respect to the body opening. The proximal point is closer to the open end of the hollow body than is the distal point. In accordance with one particular embodiment of the invention, the elliptical planar internal end wall surface has an end wall opening therein communicating with the discharge channel. The end wall opening is displaced along the major axis of the ellipse and closer to the distal point than to the proximal point. This embodiment minimizes entrapment of air bubbles adjacent the distal point on the ellipse.

The hollow body of the cartridge according to the present invention is made of a rigid, opaque plastic material. Exemplary suitable plastics include nylon-6, polypropylene and many reinforced plastics. Many other plastics will be recognized as suitable by those of skill in the art. The material is preferably opaque to wavelengths which cure or destroy the dental composite within the cartridge.

The piston may be made of the same or different material as that of the hollow body. Exemplary suitable plastics include nylon, polypropylene and many reinforced plastics. Many other plastics will be recognized as suitable by those of skill in the art.

The piston can economically be made by cutting short lengths of cylindrical dowels. According to a simple method for making the pistons of the invention, a single angled cut through a cylindrical dowel provides two identical pressure ends which can be used for two separate pistons. A simple mold shape can alternatively be employed to injection mold the piston.

Another feature of the present invention is the continuously tapering discharge nozzle. Because the outer diameter of the discharge nozzle continuously tapers from its intersection with the body to the discharge opening, and the nozzle defines a substantially cylindrical communication, the wall thickness of the discharge nozzle tapers in the direction of the discharge opening. The thickest portion of the discharge nozzle wall surrounding the cylindrical communication is adjacent the hollow body end wall. According to the invention, the discharge nozzle is designed as such to withstand the pressure exerted by the plunging piston, which will be greater near the end wall than near the discharge opening.

Although the present invention has been described in connection with preferred embodiments, it will be appreciated by those of skill in the art that additions, modifications, substitutions and deletions not specifically described may be made without departing from the spirit and scope of the invention defined in the appended claims.

We claim:

1. A dental composite cartridge for use in an ejector-type dental gun or syringe, comprising:
   a body having a generally cylindrical shape and a longitudinal axis defining a reservoir portion containing a predetermined amount of dental composite material;
   said body having a body opening at one end thereof and a laterally extending flange circumscribing said body opening;
   a planar internal end wall surface opposite said body opening and forming an angle substantially between about 30° and about 60° with respect to said longitudinal axis, and having an end wall opening therein;
   a discharge nozzle angularly disposed relative to said longitudinal axis opposite said body opening and having a distal end opening and a proximal end formed by said end wall opening, and a discharge channel extending between said distal end opening and said end wall opening to communicate with said reservoir portion; and
   a displaceable piston for sealing said body opening and having a planar pressure end surface angled relative to the longitudinal axis of said piston and parallel to said planar internal end wall surface for forcing said dental composite material through said discharge channel with displacement of piston along said longitudinal axis of said body.

2. A dental composite cartridge as claimed in claim 1, wherein said end wall opening is completely surrounded by said end wall.

3. A dental composite cartridge as claimed in claim 1, wherein said planar internal end wall surface has an elliptical shape with a major axis, the elliptically-shaped internal end wall surface intersects the generally cylindrical body at a distal point along said major axis and at a proximal point along said major axis, said proximal point is closer to said body opening than said distal point, and said end wall opening is displaced along said major axis and closer to said distal point than to said proximal point.

4. A dental composite cartridge as claimed in claim 1, wherein said cartridge comprises a molded rigid opaque plastic material.

5. A dental composite cartridge as claimed in claim 1, wherein said cartridge comprises nylon-6.

6. A dental composite cartridge as claimed in claim 1, wherein said cartridge comprises a reinforced plastic material.

7. A dental composite cartridge as claimed in claim 1, wherein said planar internal end wall surface is angled between about 40° and 50° relative to the longitudinal axis of said body.

8. A dental composite cartridge as claimed in claim 1, wherein said planar internal end wall surface is angled about 45° relative to the longitudinal axis of said body.

9. A dental composite cartridge as claimed in claim 1, wherein said discharge channel has a longitudinal axis which is substantially perpendicular to said planar internal end wall surface.

10. A dental composite cartridge as claimed in claim 1, wherein discharge nozzle defines a nozzle wall surrounding said discharge channel and having a tapering thickness in a direction from said end wall opening toward said distal end opening.

11. A dental composite cartridge as claimed in claim 1, wherein said planar internal end wall surface is angled about 45° relative to the longitudinal axis of said body, and said discharge channel has a longitudinal axis which is substantially perpendicular to said planar internal end wall surface.

12. A dental composite cartridge as claimed in claim 1, wherein said discharge nozzle is angularly disposed at about a 45° angle relative to the longitudinal axis of said body.

13. A dental composite cartridge as claimed in claim 1, wherein said planar internal end wall surface is angled about 40° to about 50° relative to the longitudinal axis of said body, said discharge channel has a longitudinal axis which is substantially perpendicular to said planar internal end wall surface, and said discharge nozzle is angularly disposed at an angle of between 40° and 50° relative to the longitudinal axis of said body.

14. A dental composite cartridge as claimed in claim 1, wherein said planar internal end wall surface is angled 45° relative to the longitudinal axis of said body, said discharge channel has a longitudinal axis which is perpendicular to said planar internal end wall surface, and said discharge nozzle is angularly disposed at a 45° angle relative to the longitudinal axis of said body.

* * * * *